United States Patent [19]

Chang

[11] Patent Number: 4,506,101
[45] Date of Patent: Mar. 19, 1985

[54] PROCESS FOR THE HYDROFORMYLATION OF OLEFINS TO PRODUCE LINEAR ALDEHYDES AND ALCOHOLS

[75] Inventor: Biau-Hung Chang, Worthington, Ohio

[73] Assignee: Ashland Oil, Inc., Ashland, Ky.

[21] Appl. No.: 414,565

[22] Filed: Sep. 2, 1982

Related U.S. Application Data

[63] Continuation-in-part of Ser. No. 332,558, Dec. 21, 1981, abandoned.

[51] Int. Cl.$^3$ ............................................. C07C 45/50
[52] U.S. Cl. .................................. 568/454; 568/451; 568/909
[58] Field of Search ...................... 568/451, 454, 909

[56] References Cited

U.S. PATENT DOCUMENTS

| | | | |
|---|---|---|---|
| 3,239,566 | 3/1966 | Slaugh et al. ...................... | 568/454 |
| 3,278,612 | 10/1966 | Greene ................................ | 568/454 |
| 3,876,672 | 4/1975 | Mrowca ............................. | 568/454 |
| 4,107,079 | 8/1978 | Chevallie et al. ................ | 252/429 R |
| 4,226,845 | 10/1980 | Laine .................................. | 423/655 |
| 4,252,678 | 2/1981 | Smith ................................ | 568/454 |
| 4,306,084 | 12/1981 | Pettit ................................. | 568/454 |
| 4,317,936 | 3/1982 | Kim et al. ......................... | 568/454 |

FOREIGN PATENT DOCUMENTS 751353 12/1970 Belgium ............................. 568/454

OTHER PUBLICATIONS

Case et al., "J. Chem Society" (1960), pp. 4632–4637.
Hieber et al., "Z. Anorga. and allge. Chemie", Band 289 (1957), 324–336.
Farmery et al., "J. Chem. Soc." (A) (1969), 2339–2345.
Hallman et al., "The Chemical Soc." (London) Chemical Communication, Apr. 12, 1967, pp. 305–306.
R. M. Laine, "Applications of the Water-Gas Shift Reaction, Hydroformylation and Hydrohydroxymethylation with CO and H$_2$O", Amer. Chem. Soc. pp. 6451–6454, 1978.
Hieber, W. et al., "Entstehung Mehrkerniger Carbonylferrate Aus Mehrkernigen Eisencarbonylen", Anorg. Allg. Chem., 1957, 289, 324–337.
Collman et al., "Oxidative-Addition Reactions of the NaFe(CO)$_4$ Supernucleophile", J. Amer. Chem. Soc., 99, 2515, 1977.
Nagel et al., "Synthesis of New Trinuclear Ions [Ru$_3$(CO)$_{11}$]$^{2-}$ and [Os$_3$(CO)$_{11}$]$^{2-}$", J. of Organometallic Chemistry, 219 (1981) C9–C12.
Eady et al., "Improved Syntheses of the Hexanuclear Clusters [Ru$_6$(CO)$_{18}$]$^{2-}$, and ... H$_2$Ru$_6$(CO)$_{18}$", 1980, J.C.S. Dalton, 383–392.
Inkrott et al., "Stepwise Deprotonation of H$_4$Ru$_4$(CO)$_{12}$: High-Yield Synthesis and Carbon-13 NMR Spectra of H$_3$Ru$_4$(CO)$_{12}^-$ and H$_2$Ru$_4$(CO)$_{12}^-$", Inorg. Chem., vol. 18, No. 10, 1979, 2817–2821.
Inkrott et al., "The New Cluster Dianion H$_2$Ru$_4$(CO)$_{12}^{2-}$. Simple High-Yield, Stepwise Deprotonation of H$_4$Ru$_4$(CO)$_{12}$", J. Amer. Chem. Soc. 100:12, Jun. 7, 1978, 3954–3955.
P. F. Jackson et al., "H$_2$Ru$_6$(CO)$_{18}$, [HRu$_6$(CO)$_{18}$]$^-$, and [Ru$_6$(CO)$_{18}$]$^{2-}$: a Simple High Yield Route to ... [Ph$_3$MeP]$_2$[Ru$_6$(CO)$_{18}$]", J.C.S. Chem. Comm., 1979, 735–736.
Nagel et al., "High Yield Syntheses of New Tetraruthenium ... of H$_2$Ru$_4$(CO)$_{13}$", J.C.S. Chem. Comm., 1980, 530–531.
A. L. Lapidus et al., "Carbonylation of Ethylene with Carbon Monoxide in the Presence of Fe Complex Catalysts", Kinetics & Catalysis, vol. 17, 1976, pp. 1274–1277.
"Effect of Carbon Monoxide Pressure ... Complex Iron Catalyst", Kinetics & Catalysts, vol. 16, 1975, pp. 214–216.

Primary Examiner—Werren B. Lone
Attorney, Agent, or Firm—Wood, Herron & Evans

[57] ABSTRACT

A process for producing linear aldehydes or alcohols from olefins using a transition metal hydroformylation catalyst wherein the catalyst comprises an anionic transition metal catalyst wherein the transition metal is Fe, Ru or Os and the catalysts generally have a charge of at least −2. The formula of the anionic catalyst is generally defined as $M^{+n}[H_yA_xL_z]^{-n}$ wherein A represents Fe, Ru or Os, M is a cationic species, n is an integer greater than or equal to 2, x is an integer greater than or equal to 1, y is an integer greater than or equal to 0 and z is an integer generally corresponding to the number of available coordination bonding sites in the ruthenium complex. Monoanionic osmium catalysts are also included within the present invention. These hydroformylation catalysts exhibit greater selectivity toward straight chained aldehydes and alcohols than anionic catalysts having a charge of −1 or a neutral catalyst. The monoanionic osmium catalyst also exhibits an increased selectivity toward the straight chain product.

The novel hydroformylation catalyst of the present invention is also disclosed.

25 Claims, No Drawings

PROCESS FOR THE HYDROFORMYLATION OF OLEFINS TO PRODUCE LINEAR ALDEHYDES AND ALCOHOLS

RELATED APPLICATION

This application is a continuation-in-part of application Ser. No. 332,558, filed Dec. 21, 1981, now abandoned, entitled Process For the Hydroformylation of Olefins Using an Improved Ruthenium Catalyst and Improved Hydroformylation Catalyst.

BACKGROUND OF THE INVENTION

The present invention relates to a process for the hydroformylation of olefins to produce aldehydes and alcohols. The present invention more particularly relates to such a process in which anionic transition metal complex catalysts are used which are extremely selective toward straight chain products. The present invention more particularly relates to the use of iron, ruthenium or osmium compounds as hydroformylation catalysts.

Aldehydes and alcohols are extremely useful as general purpose solvents, as surfactants and as precursors to many other useful chemicals. Due to the extent to which these compounds are used, it is important that such compounds be biodegradable. One important factor effecting the biodegradability of aldehydes and alcohols is the linearity of the molecule. Linear aldehydes and alcohols are more easily biodegraded than branch-chain aldehydes and alcohols. In addition, certain straight chain aldehydes and alcohols are extremely useful in particular applications.

One particular straight chain aldehyde which has particular utility is n-butyraldehyde. This aldehyde can be dehydrated to form 2-ethyl hexanol which is useful as a gasoline additive or the aldehyde can be esterified with phthalic anhydride to produce dioctylphthalate which is used for plasticizing polyvinyl chloride resins.

The straight chain alcohols or esters of the straight chain alcohols are useful as surfactants or soaps which are biodegradable. Particularly useful are $C_{12}$ and $C_{18}$ alcohols and the esters of these alcohols.

One method of producing aldehydes and alcohols is the hydroformylation of olefins. Hydroformylation is an old reaction and is used commercially to prepare both straight and branch-chain aldehydes and alcohols. In this reaction, an olefin is reduced by the addition of carbon monoxide and hydrogen to form an aldehyde. This reaction can be carried further until the aldehyde is reduced to an alcohol. This is further explained in U.S. Pat. No. 3,876,672 which is incorporated herein by reference.

The hydroformylation reaction generally requires a catalyst. In the past, typical catalysts have included cobalt carbonyl, rhodium carbonyl, nickel, and platinum complexes, as well as monovalent ruthenium cluster complexes. A problem encountered with most of these prior art catalysts was the low percentage of linear aldehydes or alcohols produced. Never has it been appreciated that iron and ruthenium compounds having a negative charge of greater than or equal to two, and osmium catalysts having a negative charge of greater than or equal to 1, provide a means to selectively obtain linear aldehydes and alcohols.

Therefore, it is an object of the present invention to disclose a process for the hydroformylation of olefins to produce a high percentage of linear aldehydes or alcohols and low percentage of branch-chain aldehydes or alcohols.

SUMMARY OF THE INVENTION

The present invention comprises a method of forming aldehydes according to the following reaction:

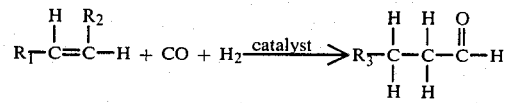

wherein the catalyst has the following general formula:

wherein:
A represents Fe, Ru or Os;
M represents a cationic moiety; n represents an integer greater than or equal to 2 when A is Fe or Ru, and n represents an integer greater than or equal to 1 when A represents Os;
y represents an integer greater than or equal to 0;
x represents an integer greater than or equal to 1;
L represents a ligand; and
z represents an integer less than or equal to the number of available coordination bonding sites of the transition metal complex. This reaction can be carried further whereby the aldehyde is reduced to form an alcohol.

DETAILED DESCRIPTION OF THE INVENTION

The hydroformylation reaction is an addition reaction in which carbon monoxide and hydrogen are reacted with an olefin to produce a saturated aldehyde. In other words, carbon monoxide and hydrogen are added to the olefin and the olefin reduced. The olefin can be reacted with carbon monoxide in the presence of hydrogen and a catalyst, or the olefin can be reacted with an excess of carbon monoxide and water in the presence of a catalyst. When carbon monoxide and water are used in the reaction, the water is simply a source of hydrogen, reacting with the carbon monoxide to form hydrogen and carbon dioxide. Hydrogen is thereby provided to react together with carbon monoxide upon the olefin. In either case, there is a hydrogen source available to react in combination with carbon monoxide upon the olefin. This reaction can be continued and available hydrogen would react with the aldehyde to produce an alcohol. The formation of the alcohol is encouraged by altering reaction conditions such as reaction time, pressure and temperature.

The hydroformylation reaction is shown by the following reaction formula (I):

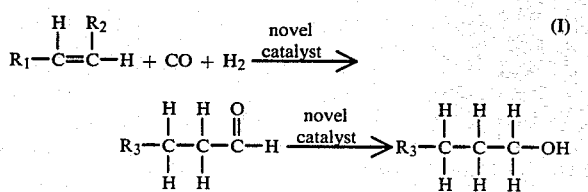

wherein $R_1$ represents alkyl, substituted alkyl, aryl or substituted aryl and $R_2$ represents hydrogen, alkyl, substituted alkyl, aryl or substituted aryl. As shown in formula (I), this reaction can be carried further causing the addition of hydrogen to the formed aldehyde forming a linear alcohol.

Even if when $R_2$ is not hydrogen, the novel catalyst of the present invention will cause the double bond in the olefin reactant to migrate to form a linear aldehyde. $R_1$ or $R_2$ must, however, be either hydrogen or an unsubstituted alkyl group or the reaction will proceed at a very slow rate. $R_3$ will represent alkyl, substituted alkyl, aryl or substituted aryl and its formula will be determined by the make-up of $R_1$ and $R_2$. Thus, for example, if $R_1$ and $R_2$ are methyl groups, the hydroformylation will produce an aldehyde in which $R_3$ is an ethyl group. The double bond in the olefin will have migrated one carbon atom to form n-pentaldehyde.

The hydroformylation reaction is applicable to a wide variety of unsaturated compounds, including compounds containing more than one ethylenic group. Since difficulty has been experienced where the olefin is highly branched, two substituents of the olefinic group should be hydrogen as is shown in formula I. Hydroxyl or halogen substituents must be removed from the double bond by at least two carbon atoms and preferably not be present at all since they inactivate the catalyst in some situations.

Substituents which do not substantially interfere with the hydroformylation reaction include alkyl, aryl carbonyl, aryl, $C_1$–$C_9$ alkoxycarbonyl, aralkyl, $C_1$–$C_9$ alkaryl, $C_1$–$C_9$ alkoxy and aryloxy. Aryl groups present may also be substituted by any of the other non-interfering substituents. The unsaturated compounds may contain up to 20 carbon atoms.

In order to obtain the full benefit of the present invention, $R_1$ and $R_2$ should be a straight chain $C_1$–$C_9$ alkyl group or $R_1$ or $R_2$ should be hydrogen. If $R_1$ and $R_2$ would be hydrogen, the product must necessarily be straight chain, i.e., propanal. Therefore, if ethylene is the olefin reactant, the benefit of using the catalyst of the present invention is not appreciated. When ethylene is reacted, a more reactive catalyst which is not selected toward the linear product should be used.

The preferred olefin of the present invention should have the following general formula:

(II)

wherein $R_4$ is a straight chain $C_1$–$C_{18}$ alkyl. This olefin should react quickly with high selectivity toward linear product.

In the event a di-olefin were reacted to form a dialdehyde or dialcohol, the olefin should have the following general Formula III.

(III)

wherein $R_5$ is an alkyl, substituted alkyl, aryl or substituted aryl, and preferably, a straight chain $C_1$–$C_9$ or higher alkyl.

Preferred olefins include: propylene, butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadecene-1, nonadecene-1, eicosene, 1,5-hexadiene, 1,6-heptadiene, 1,7-octadiene, 1,8-nonadiene, 1,9-decadiene, 1,10-undecadiene, and 1,11-dodecadiene.

Novel Catalysts

The catalysts of the present invention are anionic transition metal complex molecules. The general formula of the anionic transition metal complex molecules which form the novel hydroformylation catalysts of the present invention is:

(IV)

wherein A represents Fe, Ru and Os, M is a cationic species, n is an integer greater than or equal to 2 when A is Fe or Ru and n is an integer greater than n equal to 1, when A is Os, x is an integer greater than or equal to 1, y is an integer greater than or equal to 0, and z is an integer less than or equal to the available coordination bonding sites of the transition metal complex represented by $A_x$.

Typically n will not exceed 6, y will not exceed 4 and is usually 2 or less, x will not exceed about 6. In theory these upper limits may be exceeded, but known species generally fall within these limits. The ligands represented by L include any ligand which will bond with the transition metal complexes and which will not interfere with the hydroformylation reaction. Ligands specifically suitable for use in the present invention include: trialkyl phosphines, trialkyl arsines, trialkyl antimonies, trialkyl bismuths, triaryl phosphines, triaryl arsines, triaryl antimonies, triaryl bismuths, carbon monoxide and tertiary amines.

M can represent any cationic species which will bond to the transition metal anionic complex and will not interfere with the hydroformylation reaction. Generally, M will be a metal and preferably selected from Group IA and Group IIA or an organic cation such as iminium, ammonium, phosphonium or arsenium.

The methods used to make the catalysts of the present invention are well known to those of ordinary skill in the art. This is indicated by the numerous articles cited hereinafter.

The catalysts of the present invention can be prepared by the reduction of the neutral species such as metal carbonyls or by the deprotonization of hydride metal compounds.

For example, $[(Ph_3P)_2N]_2[Fe_3(CO)_{11}]$ can be prepared from $Fe_3(CO)_{12}$. More specifically, the $Fe_3(CO)_{12}$ can be reacted with KOH dissolved in absolute methanol at room temperature for about 28 hours. The addition of $(Ph_3P)NCl$ causes $[(Ph_3P)_2N]_2[Fe_3(CO)_{11}]$ to precipitate out of solution. This is further described in Hieber, W.; Brendel, G. Z., *Anorg. Allg. Chem.*, 1957, 289, 324–337.

As discussed in Collman et al, *Oxidative-Addition Reactions of the $NaFe(CO)_4$ Supernucleophilic*, J. American Chem. Soc., 94, 2515 (1977), $Na_2Fe(CO)_4$ and analogous compounds can be prepared by the reduction of $Fe(CO)_5$ using sodium dispersed in benzophenone. $K_2Fe(CO)_4$ can be prepared in a similar manner.

Specific iron catalysts which are useful in the present invention include:

$M^{+2}Fe(CO)_4^{-2}$ $M^{+2}Fe_2(CO)_8^{-2}$ $M^{+2}Fe_3(CO)_{11}^{-2}$ $M^{+2}Fe_4(CO)_{13}^{-2}$

Osmium catalysts useful in the present invention have the following general formula:

$$M^{+n}[H_yOs_xL_z]^{-n}$$

where n is an integer greater than or equal to 1. With ruthenium and iron, the charge on the anionic transition metal moiety must be at least −2. However, with osmium, a charge of −1 still provides excellent selectivity toward linear product wherein the neutral osmium species does not.

Again, the compounds used as catalysts of the present invention and the methods of preparation are generally well known to those of ordinary skill in the art. For example, the preparation of $[Os_3(CO)_{11}]^{2-}$ is discussed in Nagel et al, *Synthesis of New Trinuclear Ions $[Ru_3(CO)_{11}]^{2-}$, and $[Os_3(CO)_{11}]^{2-}$* in *J. of Organometallic Chemistry*, 219 (1981) C9-C12. These catalysts are prepared by the reduction of the neutral species using, for example, an alkali metal benzophenone solution.

Osmium compounds useful as catalysts in the present invention include:

$M^{2+}Os_3(CO)_{11}^{2-}$ $M^{1+}HOs_3(CO)_{11}^{1-}$ $M^{2+}Os(CO_4)^{2-}$

The anionic ruthenium catalyst of the present invention may be produced according to numerous methods disclosed in the following articles: Eady et al, *Improved Synthesis of the Hexanuclear Clusters $[Ru_6(CO)_{18}]^{2-}$, $[HRu_6(CO)_{18}]^-$, and $H_2Ru_6(CO)_{18}$*, 1980 J. C. S. Dalton, 383; Inkrott et al, *Stepwise Deprotonation of $H_4Ru_4(CO)_{12}$: High-Yield Synthesis and Carbon-13 NMR Spectra of $H_3Ru_4(CO)_{12}^-$ and $H_2Ru_4(CO)_{12}^{2-}$*, 18 Inorganic Chemistry 2817 (1979); Inkrott et al, *The New Cluster Dianion $H_2Ru_4(CO)_{12}^{2-}$*, 100:12 Journal of the American Chemical Society 3954(1978); P. F. Jackson et al, $H_2Ru_6(CO)_{18}$,$[HRu_6(CO)_{18}]^-$ and $[Ru_6(CO)_{18}]^{2-}$: *A Simple High Yield Route to These Clusters and the X-Ray Structure of $[Ph_3MeP]_2[Ru_6(CO)_{18}]$*, J.C.S. Chem. Com., 735 (1979); Nagel et al, *High Yield Synthesis of New Tetraruthenium Carbonylates: $[Ru_4(CO)_{13}]^{2-}$, $[HRu_4(CO)_{13}]^-$, and $[Ru_4(CO)_{12}]^{4-}$*, J.C.S. Chem. Com., 530 (1980); which are incorporated herein by reference to indicate the state of the art in ruthenium complex chemistry.

The catalyst of the present invention can be formed, for example, by the stepwise deprotonation of $H_4Ru_4(L)_z$ according to the following formula:

$$H_4Ru_4(L)_z + 2KH \xrightarrow{THF} K_2^{2+}[H_2Ru_4(L)_z]^{2-} \quad \text{(V)}$$

wherein L represents a ligand and z is an integer corresponding to the number of available coordination bonding sites. When $H_2Ru_4(CO)_{12}^{2-}$ is being formed, the reaction is conducted by mixing the KH with the $H_4Ru_4(CO)_{12}$ in THF for about one half an hour at 55° C. and an additional 24 hours at ambient temperatures, both in an inert atmosphere. Removal of the solvent in vacuo yields $K_2[H_2Ru_4(CO)]_{12}$. The reaction product can be further reacted with two equivalents of $[(Ph_3P_2)N]Cl$ or $[(n-C_4H_9)_4N]Br$ to produce $[(Ph_3P)_2N]^{+2}_2[H_2Ru_4(CO)_{12}]^{-2}$ and $[(n-C_4H_9)_4N]^{+2}_2[H_2Ru_4(CO)_{12}]^{2-}$, respectively.

Another method of producing the catalysts of the present invention is the controlled reduction of $Ru_3(L)_z$ using potassium-benzophenone according to the following reaction:

$$4Ru_3(L)_z + 6KPh_2CO \rightarrow 3K_2[Ru_4(L)_z] + 6Ph_2CO \quad \text{(VI)}$$

The reaction should be conducted in a dry, inert atmosphere, such as argon or nitrogen. A more specific example is the reduction of dodecarbonyltriruthenium by treatment with 1.6 equivalents of potassium-benzophenone (10% excess) in THF. A deep red solution is produced after stirring the solution overnight at −78° C. and for 24 hours at 25° C. $K_2[Ru_4(CO)_{13}]$ is then obtained from this solution by precipitation with $CH_2Cl_2$. The deep red reaction mixture can be further reacted with $[(Ph_3P)_2N]Cl$ and precipitated with $CH_2Cl_2$ to yield $[(Ph_3P)_2N]_2[Ru_4(CO)_{13}]$.

A tetravalent ruthenium salt $K_4[Ru_4(CO)_{12}]$ can also be formed in a similar manner according to the following reaction formula:

$$4Ru_3(CO)_{12} + 12KPh_2CO \longrightarrow \quad \text{(VII)}$$
$$3K_4[Ru_4(CO)_{12}] \text{(solid)} + 12CO + 12Ph_2CO$$

$K_4[Ru_4(CO)_{12}]$ can also be produced by the direct reduction of $K_2[Ru_4(CO)_{13}]$ according to the following reaction:

$$K_2[Ru_4(CO)_{13}] + 2KPh_2CO \longrightarrow \quad \text{(VIII)}$$
$$K_4[Ru_4(CO)_{12}] \text{(solid)} + CO + 2Ph_2CO.$$

Divalent hexaruthenium compounds can be formed by reacting a triruthenium compound such as dodecarbonyltriruthenium in aqueous THF with KOH forming $K_2[Ru_6(CO)_{18}]$.

There are other methods to produce ruthenium complex anions which have a negative charge of at least 2. These methods are generally known to those of ordinary skill in the art.

Specific ruthenium catalysts useful in the present invention include:

$M^{2+}Ru_6(CO)_{18}^{2-}$ $M^{2+}Ru_4(CO)_{13}^{2-}$ $M^{2+}H_2Ru_2(CO)_{12}^{4-}$ $M^{2+}Ru(CO)_4^{2-}$

As will become apparent from the examples provided herein, particularly good results are obtained when the ruthenium catalyst has more than one ruthenium atom present in the molecule. More specifically, ruthenium cluster molecules in which two or more ruthenium atoms are bonded to each other, are preferred.

These iron, osmium and ruthenium catalyst can also be prepared in the reactor without isolating the catalyst. In this modified process, the catalyst precursor, i.e., a neutral or monoanionic ruthenium or iron compound or a neutral osmium compound is placed in a reactor. A strong reducing agent dissolved in an appropriate anhydrous solvent is also added to the reactor and allowed to react at desired temperatures, −90° C.-180° C., for a few minutes to about 24 hours. The olefin reactant is added and the pressure in the reactor is increased to about 500 to 2500 psig by injecting a one to one molar ratio of carbon monoxide and hydrogen. The temperature within the reaction vessel is raised to about 80°-200° C., and the reactants agitated. After the desired reaction time, usually 0.5 to about 10 hours, the produced aldehyde or alcohol is separated by known methods.

Suitable catalyst precursors include $Ru_3(CO)_{12}$, $H_4Ru_4(CO)_{12}$, $H_2Ru_4(CO)_{13}$, $Os_3(CO)_{12}$, and $Fe(CO)_5$. Suitable reducing agents include potassium hydride, lithium borohydride, sodium borohydride, alkali metal alkyl borohydride and tri-sec-butyl borohydride, and alkali metal-benzophenone.

The ratio of reducing agent to catalyst precursor can vary from 1 to 20. Preferably, the reducing agent and the catalyst precursor are dissolved in a suitable solvent, preferably an aprotic polar solvent such as anhydrous THF.

By this method, the catalyst can be formed in the reactor and the catalyst need not be isolated. This reaction can also be conducted in a continuous reactor by packing the reactor with the catalyst precursor and injecting the reducing agent dissolved in an appropriate solvent through the reactor. The reactants can be added along with the reducing agent or can be added after the addition of the reducing agent is discontinued. The flow of reducing agent should be continued until the desired selectivity toward linear product is obtained or until the selectivity ceases to improve. The length of time will vary depending on the catalyst and the reducing agent.

This method of preparing the catalyst should be conducted in a substantially anhydrous environment. The reducing agent, if dissolved in water, increases the pH of the system to such an extent that aldol condensation products will be formed during the hydroformylation reaction.

This method of forming the catalyst is further disclosed by reference to example 3.

Hydroformylation Reaction

The hydroformylation reaction is conducted by mixing the olefin, carbon monoxide, and a hydrogen source, i.e., hydrogen or water together with the catalyst, and optionally, a solvent in a continuous or batch-type reactor. Preferably, the solution is heated and maintained under increased pressure.

While the reaction will occur at room temperature, it is preferred to heat and maintain the solution at 120°-200° C. In general, if the temperature is decreased, the rate of the reaction decreases. But, as the temperature is increased above 200° C., the selectivity toward linear aldehydes and alcohols decreases. In addition, the increase in temperature increases the difficulty of controlling the reaction to obtain primarily aldehydes as opposed to alcohols should this be desired.

Preferably, for the production of straight chain aldehydes, the pressure of the reaction should be maintained at between 500 psi to 2500 psi. This combined with a mixing force causes the carbon monoxide to go into solution. The higher pressure also tends to increase both the reaction rate and the selectivity of the reaction toward linear products. However, increased pressure also promotes the continuation of the reaction to produce alcohols.

The reaction time will vary depending on the temperature and pressure. Generally, the reaction time is maintained between 0.5–10 hours. An increase in time will cause an increase in the production of alcohol. It should be noted that in order to obtain only linear aldehydes, the reaction time is kept to a minimum which in turn does not provide time for most of the olefin to react. This can be more fully appreciated by considering the examples provided below.

To increase the production of alcohol as opposed to the aldehyde, the reaction temperature should be above 160° C.; the pressure should be above 800 psi and the reaction time from 3–5 hours or longer. Analysis of the reaction products will enable one of ordinary skill in the art to select the preferred reaction conditions for a particular olefin and catalyst.

The reaction may be run with or without a solvent. Suitable solvents include aldehydes, alcohols, ethers, esters, ketones, nitriles, aromatic hydrocarbons, aliphatic hydrocarbons, and chlorocarbons. Particularly suitable solvents include tetrahydrofuran, dibutyl ether, diethyl ether, dioxane, 2-methoxyethyl ether, 1,2-dimethoxyethane, butyl alcohol, ethyl alcohol, ethylene glycol, isobutyl alcohol, n-butyraldehyde, ethyl acetate, amyl acetate, ethyl butyrate, methyl benzoate, acetone, methyl ethyl ketone, methyl isobutyl ketone, acetonitrile, propionitrile, benzonitrile, chloroform, ethylene dichloride, methylene chloride, chlorobenzene, the chlorotoluenes, benzene, toluene, xylene, hexane, heptane, octane, cyclohexane, and methylcyclohexane.

The reaction can be conducted in a continuous or batch-type reactor. Only the batch-type reaction is described below. However, this will enable one of ordinary skill in the art to perform the hydroformylation reaction in a continuous reactor.

The reaction is conducted by charging the olefin, the catalyst and the solvent into an autoclave reaction vessel which is provided with a mixer. The reaction vessel is thoroughly flushed with carbon monoxide and then pressurized with carbon monoxide and hydrogen. If the olefin is a gas at room temperature, it is added with the carbon monoxide and hydrogen. A sufficient quantity of each gas is added to give the desired molar ratio and the desired pressure at the chosen reaction temperature. An excess of carbon monoxide and hydrogen are generally added. Since the reaction pressure is altered by increasing or decreasing the quantity of reaction gases introduced into the reaction vessel, the preferred amount of gas is a function of the reaction pressure. The system is then heated with agitation until the reaction is complete. As the reaction proceeds, more hydrogen or carbon monoxide can be added periodically to maintain the pressure in the desired range.

If the hydrogen source is water, the above description is modified by adding water with the catalyst and hydrogen gas is not introduced. The water will react with the carbon monoxide in the presence of the catalyst to produce the needed hydrogen. This is referred to as a water-gas shift reaction.

These reactions can be further appreciated by reference to the examples provided below. These examples provide evidence of utility as well as a comparison between the method of the present invention and methods not included within the scope of this invention. Attention should be focused on the selectivity toward the linear product obtained using either type of catalyst. As can be seen by looking at these examples, the specificity toward a linear product is substantially improved when a catalyst of the present invention is used.

EXAMPLE 1

In a 300 ml. stainless steel autoclave reactor 0.096 g. (0.044 mmol) of [(PH$_3$P)$_2$N]$_2$Ru$_6$(CO)$_{18}$, 0.5 ml. (4.57 mmol) of 1-pentene and 80 ml. of anhydrous THF were mixed under argon. The autoclave was flushed twice with argon, three times with carbon monoxide, then charged to 1550 psig pressure with CO and H$_2$ (1:1). The autoclave with magnetic driven stirrer was heated up to 160° C. using an automatic controlled electric heater, and the pressure was increased to 1850 psig. After being stirred at 160° C. for 1.5 hours, the pressure changed from 1850 psig to 1800 psig. The autoclave was cooled down to room temperature and opened under argon. The reaction products were analyzed using gas chromatography. The pentene (13.5%) was converted into n-hexanal (96.9%), and 2-methylpentanal (3.1%).

EXAMPLE 2

Catalytic Runs Using CO/H$_2$O:

0.0963 g. (0.071 mmol) of (Bu$_4$N)$_2$Os$_3$(CO)$_{11}$, 10 ml. (556 mmol) of distilled water, 3 ml. (19.1 mmol) of 1-octene, and 70 ml. of THF were mixed in a 300 ml. autoclave. The autoclave was flushed five times with CO, then charged to 1700 psig with CO. The reactor was heated to 180° C. and the pressure was increased to 2200 psig. After being stirred at 180° C. for 3 hours, the autoclave was cooled to room temperature. A brown THF solution formed and was analyzed using a gas chromatograph. It was found that octene (1.4%) was converted into n-nonanal with a very high selectivity (91.2%).

EXAMPLE 3

Ruthenium carbonyl (Ru$_3$(CO)$_{12}$), 0.100 g (0.16 mmol), 1.6 mmol of potassium tri-sec-butylborohydride (KHB(sec-Bu)$_3$), and 90 ml of anhydrous THF were placed in a 300 ml hastelloy C autoclave reactor. The reactor is sealed, flushed three times with argon, pressurized with 80 psig of argon, and heated to 180° C. with stirring. After being heated at 180° C. for five hours, the reactor is cooled. The tri-ruthenium dodecarbonyl is orange in color. However, during the reaction, there is a color change to red-brown, indicating that the ruthenium has been reduced and most of the ruthenium complex is in the form of a dianion. Without separating the by-products, di-n-butyl ether (0.54 g) (as internal standard) and 1-pentene (2 ml, 18 mmol) were then introduced into the reactor. The autoclave was pressurized with 1600 psig of an approximately equimolar mixture of carbon monoxide and hydrogen, and heated to 160° C. with stirring. The reaction was allowed to proceed for one hour. The reactor was next cooled and the reaction products drawn out. G. C. analysis indicated that 9% of the 1-pentene was reacted with a linear selectivity of 93%.

In the following examples shown in Tables 1-3 below, the hydroformylation reaction was conducted in a 300 ml. carpenter 20 CB/hastelloy C autoclave which was charged with the specified amount of catalyst and 0.5 ml. (4.6 mmol.) of 1 pentene, about 0.55 g. of di-n-butyl ether (as an internal standard) and 80 ml. of anhydrous THF. This was flushed with carbon monoxide and pressurized with CO/H$_2$ and heated as indicated in the tables. As shown in the table, the dianionic ruthenium catalyst substantially outperformed the neutral or monoanionic catalyst, particularly with respect to product linearity. "n/i ratio" represents the ratio of linear to branch chain products.

TABLE 1

HYDROFORMYLATION OF 1-PENTENE CATALYZED BY H$_4$Ru$_4$(CO)$_{12}$ AND ITS ANIONS

| Catalyst[a] (mmol) | Reaction[b] Conditions | Reaction Time | Conversion | Selectivity Linear Aldehyde | Selectivity Branched Aldehyde | n/i ratio |
|---|---|---|---|---|---|---|
| H$_4$Ru$_4$(CO)$_{12}$ | CO/H$_2$ (1:1) | 1 hr | 13.4% | 85.4% | 14.6% | 5.85 |
| (0.090 mmol) | Pr.t. = 1600 | 3 hr | 21.2% | 82.9% | 17.1% | 4.85 |
| (Neutral) | psig | 6 hr | 27.9% | 80.1% | 19.9% | 4.03 |
|  | 1950~1940 psig | 10 hr | 31.8% | 77.8% | 22.2% | 3.50 |
|  | 160° C. in THF |  |  |  |  |  |
| (PNP) H$_3$Ru$_4$(CO)$_{12}$ | CO/H$_2$(1:1) | 1 hr | 14.0% | 90.0% | 10.0% | 9.0 |
| (0.090 mmol) | Pr.t = 1600 psig | 3 hr | 33.1% | 87.0% | 13.0% | 6.69 |
| (Monoanionic) | 1950~1900 psig | 6 hr | 41.9% | 84.9% | 15.1% | 5.62 |
|  | 160° C. in THF | 10 hr | 46.7% | 83.8% | 16.2% | 5.17 |
| (PNP)$_2$H$_2$Ru$_4$(CO)$_{12}$ | C0/H$_2$ (1:1) | 1 hr | 24.2% | 97.1% | 2.9% | 33.48 |
| (0.093 mmol) | Pr.t = 1600 psig | 3 hr | 44.8% | 97.0% | 3.0% | 32.33 |
| (Dianionic) | 1950~1900 psig | 6 hr | 56.4% | 97.4% | 2.6% | 37.46 |
|  | 160° C. in THF | 10 hr | 61.1% | 96.8% | 3.2% | 30.25 |
| (PNP)$_2$H$_2$Ru$_4$(CO)$_{12}$ | CO/H$_2$ (1:1) | 1 hr | 5.8% | 96.3% | 3.7% | 26.03 |
| (0.038 mmol) | Pr.t. = 1600 psig | 3 hr | 8.6% | 91.1% | 8.9% | 10.24 |
| (Dianionic) | 1950~1900 psig | 6 hr | 12.2% | 89.4% | 10.6% | 8.43 |
|  | 160° C. in THF | 10 hr | 17.0% | 86.8% | 13.2% | 6.58 |
|  | 1-pentene (triple) |  |  |  |  |  |
| H$_4$Ru$_4$(CO)$_9$(PBu$_3$)$_3$ | CO/H$_2$(1:1) | 1 hr | 1.0% | 86.0% | 14.0% | 6.14 |
| (0.170 mmol) | Pr.t. - 1600 psig | 3 hr | 10.0% | 79.6% | 20.4% | 3.90 |
| (Neutral) | 1920~1750 psig | 6 hr | 17.0% | 77.5% | 22.5% | 3.44 |
|  | 160° C. in THF | 13 hr | 28.3% | 74.6% | 25.4% | 2.94 |

[a]PNP = bis(triphenyl phospine) iminium.
[b]Pr.t. = pressures at room temperature.

TABLE 2

HYDROFORMYLATION OF 1-PENTENE CATALYZED BY $H_2Ru_4(CO)_{13}$ AND ITS ANIONS

| Catalyst (mmol) | Reaction Conditions | Reaction Time | Conversion | Selectivity Linear Aldehyde | Selectivity Branched Aldehyde | n/i ratio |
|---|---|---|---|---|---|---|
| $H_2Ru_4(CO)_{13}$ | $CO/H_2$ (1:1) | 1 hr | 5.0% | 82.2% | 17.8% | 4.62 |
|  | Pr.t. = 1600 psig | 3 hr | 8.4% | 80.9% | 19.1% | 4.24 |
| (0.058 mmol) | 1810~1710 psig | 6 hr | 13.5% | 78.8% | 21.2% | 3.72 |
| (Monoanionic) | 160° C. in THF | 21.25 hr | 19.2% | 75.0% | 25.0% | 3.00 |
| $(PNP)HRu_4(CO)_{13}$ | $CO/H_2$ (1:1) | 1 hr | 14.0% | 75.7% | 24.3% | 3.12 |
|  | Pr.t. = 1600 psig | 3 hr | 34.8% | 75.3% | 24.7% | 3.05 |
| (0.058 mmol) | 1890~1800 psig | 6 hr | 49.9% | 73.3% | 26.7% | 2.75 |
| (Neutral) | 160° C. in THF | 10 hr | 52.8% | 71.0% | 29.0% | 2.45 |
| $(PNP)HRu_4(CO)_{13}$ | $CO/H_2$ (1:1) | 1 hr | 45.4% | 73.2% | 26.8% | 2.73 |
|  | Pr.t. = 1600 psig | 3 hr | 49.7% | 74.5% | 25.5% | 2.92 |
| (0.066 mmol) | 1900~1850 psig | 5.5 hr | 53.1% | 74.0% | 26.0% | 2.85 |
| (Monoanionic) | 160° C. in THF |  |  |  |  |  |
| $(PNP)_2Ru_4(CO)_{13}$ | $CO/H_2$ (1:1) | 1 hr | 27.3% | 97.5% | 2.5% | 39.0 |
|  | Pr.t. = 1600 psig | 3 hr | 48.3% | 97.2% | 2.8% | 34.71 |
| (0.057 mmol) | 1900~1820 psig | 6 hr | 53.4% | 96.3% | 3.7% | 26.03 |
| (Dianionic) | 160° C. in THF | 10 hr | 60.7% | 96.2% | 3.8% | 25.32 |
| $(PNP)_2Ru_4(CO)_{13}$ | $CO/H_2$ (1:1) | 2 hr | 22.2% | 91.0% | 9.0% | 10.11 |
|  | Pr.t. = 1600 psig | 4 hr | 34.9% | 86.0% | 14.0% | 6.14 |
| (0.006 mmol) | 1950~1900 psig | 6 hr | 39.4% | 80.7% | 19.3% | 4.18 |
| (Dianionic) | 160° C. in THF | 29 hr | 54.7% | 72.5% | 27.5% | 2.64 |

TABLE 3

HYDROFORMYLATION OF 1-PENTENE CATALYZED BY $H_2Ru_6(CO)_{18}$ AND ITS ANIONS

| Catalyst (mmol) | Reaction Conditions | Reaction Time | Conversion | Selectivity Linear Aldehyde | Selectivity Branched Aldehyde | n/i ratio |
|---|---|---|---|---|---|---|
| $H_2Ru_6(CO)_{18}$ | $CO/H_2$ (1:1) | 1 hr | 16.4% | 87.7% | 12.3% | 7.13 |
|  | Pr.t. = 1600 psig | 3 hr | 19.8% | 76.4% | 23.6% | 3.24 |
| (0.044 mmol) | 1890~1800 psig | 5 hr | 24.1% | 75.4% | 24.6% | 3.07 |
| (Neutral) | 160° C. in THF | 20.75 hr | 33.3% | 71.0% | 29.0% | 2.45 |
| $(PNP)HRu_6(CO)_{18}$ | $CO/H_2$ (1:1) | 1 hr | 8.3% | 89.3% | 10.7% | 8.35 |
|  | Pr.t. = 1600 psig | 3 hr | 18.7% | 85.0% | 15.0% | 5.67 |
| (0.055 mmol) | 1990~1950 psig | 5 hr | 28.6% | 83.9% | 16.1% | 5.21 |
| (Monoanionic) | 160° C. in THF | 20.75 hr | 41.7% | 80.1% | 19.9% | 4.03 |
| $(PNP)HRu_6(CO)_{18}$ | $CO/H_2$ (1:1) | 1 hr | 13.1% | 78.4% | 21.6% | 3.63 |
|  | Pr.t. = 1600 psig | 4 hr | 33.5% | 74.2% | 25.8% | 2.88 |
| (0.015 mmol) | 2000~1800 psig | 18 hr | 36.9% | 67.1% | 32.9% | 2.04 |
| (Monanionic) | 160° C. in THF |  |  |  |  |  |
| $(PNP)_2Ru_6(CO)_{18}$ | $CO/H_2$ (1:1) | 0.5 hr | 5.6% | 99.0% | 1.0% | 99.0 |
|  | Pr.t. = 1600 psig | 1.5 hr | 13.5% | 96.9% | 3.1% | 31.26 |
| (0.044 mmol) | 1850~1750 psig | 5 hr | 30.7% | 93.6% | 6.4% | 14.62 |
| (Dianionic) | 160° C. in THF | 9 hr | 36.5% | 93.5% | 6.5% | 14.38 |
|  |  | 28.5 hr | 58.3% | 89.7% | 10.3% | 8.71 |
| $(PNP)_2Ru_6(CO)_{18}$ | $CO/H_2$ (1:1) | 1 hr | 11.2% | 99.0% | 1.0% | 99.0 |
|  | Pr.t. = 1600 psig | 3 hr | 14.2% | 99.0% | 1.0% | 99.0 |
| (0.042 mmol) | 1900~1800 psig | 4.5 hr | 18.4% | 97.3% | 2.7% | 36.0 |
| (Dianionic) | 160° C. in toluene | 11.5 hr | 36.6% | 96.1% | 3.9% | 24.6 |

Table 4 below shows the result of several reactions conducted using the tetraanion $K_4Ru_4(CO)_{12}$ and the dianion $K_2H_2Ru_4(CO)_{12}$ to catalyze the reduction of propylene in glyme. The pressures at which these reactions were carried out varied for 1700 to about 2300 psig and the temperature varied from 160° C. to about 180° C.

TABLE IV

| Catalyst | Reaction Temperature | Linear Aldehyde | Branched Aldehyde | Linear Alcohol | Branched Alcohol |
|---|---|---|---|---|---|
| $K_4Ru_4(CO)_{12}$ | 180° C. | 88.9% | 7.7% | 2.2% | 1.2% |
| $K_4Ru_4(CO)_{12}$ | 160° C. | 91.6% | 7.5% | 0.8% | 0.1% |
| $K_2H_2Ru_4(CO)_{12}$ | 180° C. | 91.2% | 7.5% | 1.1% | 0.2% |
| $(PNP)H_3Ru_4(CO)_{12}$ | 180° C. | 76.6% | 18.1% | 4.4% | 0.9% |

Table V lists additional examples, showing catalyst olefin reactant, temperature, pressure and solvent.

TABLE V

| Catalyst | Olefin mmol | Temp (°C.) | Press. PSIG | Solv. | Rxn Time (hr) | Conv. % | Selectivity (%) Linear | Selectivity (%) Brchd. |
|---|---|---|---|---|---|---|---|---|
| $(PNP)_2H_2Ru_4(CO)_{12}$ | 1-octene | 180 | 2100-2020 | THF | 2 | 44.6 | 95.9 | 4.1 |
| (0.135 mmol) | (31.8 mmol) |  |  |  | 6 | 54.6 | 96.5 | 3.4 |
| $(PNP)_2H_2Ru_4(CO)_{12}$ | 1-octene | 180 | 1000 | mono | 2 | 31.6 | 97.5 | 2.5 |
| (0.064 mmol) | (19.1 mmol) |  |  | glyme | 5 | 37.6 | 97.8 | 2.2 |
| $(PNP)_2H_2Ru_4(CO)_{12}$ | 1-octene | 180 | 1000 | mono- | 1 | 26.5 | 96.2 | 3.8 |
| (0.059 mmol) | (19.1 mmol) |  | ($CO/H_2$—3:1) | glyme | 3 | 34.2 | 95.9 | 4.1 |

TABLE V-continued

| Catalyst | Olefin mmol | Temp (°C.) | Press. PSIG | Solv. | Rxn Time (hr) | Conv. % | Selectivity (%) Linear | Brchd. |
|---|---|---|---|---|---|---|---|---|
| | | | | | 5 | 36.5 | 95.9 | 4.1 |
| (PNP)$_2$H$_2$Ru$_4$(CO)$_{12}$ (0.086 mmol) | 1-octene (19.1 mmol) | 140 | 1000 | monoglyme | 1 | 15.1 | 97.7 | 2.3 |
| | | | | | 3 | 30.5 | 98.0 | 2.0 |
| | | | | | 5 | 40.0 | 98.1 | 1.9 |
| (PNP)$_2$H$_2$Ru$_4$(CO)$_{12}$ (0.081 mmol) | 1-octene (19.1 mmol) | 200 | 500 | monoglyme | 1 | 2.4 | 92.9 | 7.1 |
| | | | | | 3 | 4.2 | 92.0 | 8.0 |
| | | | | | 5 | 4.7 | 92.2 | 7.8 |
| (PNP)$_2$H$_2$Ru$_4$(CO)$_{12}$ (0.076 mmol) | 1-octene (19.1 mmol) | 180 | 1500 | monoglyme | 1 | 26.2 | 47.1 | 2.9 |
| | | | | | 3 | 36.4 | 96.6 | 3.4 |
| | | | | | 5 | 38.7 | C$_8$CHO 96.1 | 3.6 |
| | | | | | | | C$_9$OH 0.3 | — |
| (PNP)$_2$H$_2$Ru$_4$(CO)$_{12}$ (0.056 mmol) | 1-octene (19.1 mmol) | 140 | 500 | monoglyme | 1 | 13.6 | 97.7 | 2.3 |
| | | | | | 3 | 19.6 | 97.4 | 2.6 |
| | | | | | 5 | 26.3 | 97.4 | 2.6 |
| (PNP)$_2$H$_2$Ru$_4$(CO)$_{12}$ (0.072 mmol) | 1-octene (19.1 mmol) | 180 | 1000 | Tetrahydropyran (undistilled) | 1 | 7.0 | C$_8$CHO 72.8 | 15.2 |
| | | | | | | | C$_9$OH 9.6 | |
| | | | | | 3 | 5.2 | C$_8$CHO 42.2 | 2.4 |
| | | | | | | | | 26.2 |
| | | | | | | | C$_9$OH 26.7 | 5.0 |
| | | | | | 5 | 5.5 | C$_8$CHO 44.6 | 26.7 |
| | | | | | | | C$_9$OH 22.8 | 5.9 |
| (PNP)$_2$H$_2$Ru$_4$(CO)$_{12}$ (0.075 mmol) | 1-octene (19.1 mmol) | 140 | 500 (CO/H$_2$—3:1) | monoglyme | 1 | 7.4 | 98.2 | 1.8 |
| | | | | | 3 | 21.2 | 97.5 | 2.5 |
| | | | | | 5 | 32.5 | 97.6 | 2.4 |
| (PNP)$_2$H$_2$Ru$_4$(CO)$_{12}$ (0.068 mmol) | 1-octene (19.1 mmol) | 140 | 500 | diglyme | 1 | 10.7 | 99.3 | 0.7 |
| | | | | | 3 | 31.4 | 98.0 | 1.0 |
| | | | | | 5 | 34.8 | 99.1 | 0.9 |
| (PNP)$_2$H$_2$Ru$_4$(CO)$_{12}$ (0.066 mmol) | 1-octene (19.1 mmol) | 140 | 500 | diethoxyethane | 1 | 2.0 | 99.0 | 1.0 |
| | | | | | 3 | 8.2 | 98.5 | 1.5 |
| | | | | | 5 | 16.0 | 98.5 | 1.5 |
| (PNP)$_2$H$_2$Ru$_4$(CO)$_{12}$ (0.079 mmol) | 1-octene (19.1 mmol) | 180 | 1000 | diethoxyethane | 1 | 10.8 | 97.2 | 2.8 |
| | | | | | 3 | 27.4 | C$_8$CHO 96.8 | 2.9 |
| | | | | | | | C$_9$OH 0.3 | |
| | | | | | 5 | 33.1 | C$_8$CHO 96.2 | 3.2 |
| | | | | | | | C$_9$OH 0.6 | — |
| K$_2$H$_2$Ru$_4$(CO)$_{12}$ (0.115 mmol) | 1-octene (19.1 mmol) | 140 | 500 | monoglyme | 1 | 4.9 | 98.5 | 1.5 |
| | | | | | 3 | 15.0 | C$_8$CHO 97.6 | 1.6 |
| | | | | | | | C$_9$OH 0.7 | — |
| | | | | | 5 | 19.8 | C$_8$CHO 97.8 | 1.8 |
| | | | | | | | C$_9$OH 0.5 | — |

Table VI shows examples using the osmium catalysts.

TABLE VI

| Catalysts | React. Cond. | React. Time | Conver. | Selectivity Lin. Ald. | Brchd. Ald. |
|---|---|---|---|---|---|
| (Bu$_4$N)$_2$Os$_3$(CO)$_{11}$ (0.127 mmol) | 1-octene (19.1 mmol) CO/H$_2$ (1:1) 1000 psig at 180° C. in glyme | 1 hr. | 1.6% | 96.2% | 3.8% |
| | | 5 hr. | 4.6% | 92.3% | 7.7% |
| (Bu$_4$N)HOs$_3$(CO)$_{11}$ (0.078 mmol) | 1-octene (19.1 mmol) CO/H$_2$ (1:1) 1000 psig at 180° C. in glyme | 1 hr. | 1.8% | 93.3% | 6.7% |
| | | 3 hr. | 2.2% | 89.5% | 10.5% |
| (Bu$_4$N)$_2$Os$_3$(CO)$_{11}$ (0.071 mmol) | 1-octene (19.1 mmol) COH$_2$O 2200 psig at 180° C. in glyme | 3 hr. | 1.4% | 91.2% | 8.8% |
| H$_2$Os$_3$(CO)$_{11}$ | 1-octene (19.1 mmol) 1000 psig CO/H$_2$ (1:1) 180° C. in 1,2-dimethoxyethane | 3 hr. | 2.0% | 83.8% | 16.2% |

The experiment using H$_2$Os$_3$(CO)$_{11}$ is a comparative example. This demonstrates the poorer selectivity towards linear product which is obtained when a neutral osmium catalyst is employed.

Table VII shows examples using iron catalysts.

TABLE VII

| Catalyst | React. Cond. | React. Time | Conver. | Selectivity Lin. Prod.* | Brchd. Prod.* |
|---|---|---|---|---|---|
| Na₂Fe(CO)₄ (1.334 mmol) | 1-pentene (18.3 mmol) COH₂ (1:1) 1980 psig at 180° C. in THF | 5 hr. | 4.5% | 82.2% | 17.8% |
| Na₂Fe(CO)₄ (2.32 mmol) | 1-octene (19.1 mmol) CO/H₂ (1:1) 2310 psig at 160° C. in glyme | 6 hr. | 1.0% | 87.4% | 12.6% |
| [(Ph₃P)₂N]₂Fe₂(CO)₈ (1.298 mmol) | 1-octene (19.1 mmol) CO/H₂ (1:1) 1000 psig at 160° C. in glyme | 6.5 hr. | 28.0% | 88.6% | 11.4% |
| [(Ph₃P)₂N]₂Fe₂(CO)₈ (0.35 mmol) | 1-octene (19.1 mmol) CO/H₂ (1:1) 2300 psig at 160° C. | 6 hr. | 7.2% | 85.4% | 14.6% |
| [(Ph₃P)₂N]₂Fe₃(CO)₁₁ (0.741 mmol) | 1-octene (19.1 mmol) CO/H₂ (1:1) 2340 psig at 160° C. | 6 hr. | 14.9% | 86.0% | 14.0% |

*Includes alcohols and aldehydes

Table VIII shows examples of hydroformylation with neutral and monoanionic iron catalysts.

TABLE VIII

| Catalyst | React. Cond. | React. Time | Conver. | Selectivity Lin. Ald.* | Brchd. Ald.* |
|---|---|---|---|---|---|
| Fe(CO)₅ (2.22 mmol) | 1-octene (19.1 mmol) 2390–2310 psig CO/H₂ (1:1) at 160° C. in 1,2-dimethoxyethane | 6 hr. | 10.9% | 71.4% | 28.6% |
| NaHFe(CO)₄ (2.24 mmol) | 1-octene (19.1 mmol) 2380 2290 psig CO/H₂ (1:1) at 160° C. in 1,2-dimethoxyethane | 6 hr. | 2.3% | 66.4% | 33.6% |
| Fe₃(CO)₁₂ (0.740 mmol) | 1-octene (19.1 mmol) 2360 2290 psig CO/H₂ (1:1) at 160° C. in 1,2-dimethoxyethane | 6 hr. | 12.2% | 54.1% | 45.9% |
| Fe₂(CO)₉ (0.361 mmol) | 1-octene (19.1 mmol) 2350 2300 psig CO H₂ (1:1) at 160° C. in 1,2-dimethoxyethane | 6 hr. | 7.1% | 28.6% | 71.4% |

*Includes alcohols and aldehydes.

Table VIII presents comparative examples using iron catalysts having a neutral or −1 charge. As can be seen by comparison with the examples shown in Table VII, the neutral and monoanionic iron catalysts are not nearly as selective toward linear products as the iron catalysts having a negative charge of 2 or more.

Thus, having described my invention, I claim:

1. The method of forming linear aldehydes by reacting an olefin having at least three carbon atoms with carbon monoxide and a hydrogen source in the presence of a preformed catalyst at from about 100° to about 200° C. at a pressure of from about 500 psi to about 2500 psi and from between 0.5 to about 10 hours wherein said olefin has the following general formula:

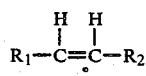

wherein $R_1$ is selected from the group consisting essentially of alkyl, substituted alkyl, aryl and substituted aryl, $R_2$ is selected from the group consisting essentially of hydrogen, alkyl, substituted alkyl, aryl and substituted aryl, and either $R_1$ or $R_2$ represents hydrogen or $C_1$-$C_9$ alkyl;

wherein said preformed catalyst has the following general formula:

wherein
A represents a metal selected from the group consisting essentially of Fe, Ru and Os;
n represents an integer greater than or equal to 2 if A is Ru or Fe and n represents an integer greater than or equal to 1 if A represents Os;
M represents a cationic moiety;
y represents an integer greater than or equal to 0;
x represents an integer greater than or equal to 1;
L is a ligand; and
z is an integer less than or equal to the available coordination bonding sites of A.

2. The method claimed in claim 1 wherein $R_2$ represents hydrogen.

3. The method claimed in claim 2 wherein $R_1$ represents $C_1$-$C_{19}$ straight chain, unsubstituted alkyl.

4. The method claimed in claim 1 wherein $R_1$ and $R_2$ represent hydrogen or $C_1$-$C_9$ straight chain, alkyl.

5. The method claimed in claim 1 wherein the hydrogen source is hydrogen gas.

6. The method claimed in claim 1 wherein A represents Os.

7. The method claimed in claim 1 wherein A represents Ru.

8. The method claimed in claim 1 wherein A represents Fe.

9. The method of forming n-butyaldehyde comprising reacting propylene with CO and hydrogen in the presence of a catalyst at from about 100° to about 200° C. at a pressure of from about 500 psi to about 2500 psi and from between 0.5 to about 10 hours, said catalyst having the following general formula:

$$M^{+n}[H_yA_xL_z]^{-n}$$

wherein
A represents a metal selected from the group consisting essentially of Fe, Ru and Os;
n represents an integer greater than or equal to 2 if A is Ru or Fe and n represents an integer greater than or equal to 1 if A is Os;
M represents a cationic moiety;
y represents an integer greater than or equal to 0;
x represents an integer greater than or equal to 1;
L is a ligand; and
z is an integer less than or equal to the available coordination bonding sites of A.

10. The method of forming linear aldehydes comprising reacting an olefin, carbon monoxide and hydrogen in the presence of a catalyst at from about 100° to about 200° C. at a pressure of from about 500 psi to about 2500 psi and from between 0.5 to about 10 hours wherein said catalyst has the following general formula:

$$M^{+n}[H_yOs_xL_z]^{-n}$$

wherein
M represents a cationic moiety;
n represents an integer greater than or equal to 1;
y represents an integer greater than or equal to 0;
x represents an integer greater than or equal to 1;
L is a ligand; and
z represents an integer less than or equal to the available coordination bonding sites of the Os.

11. The method of forming linear aldehydes comprising reacting an anhydrous mixture comprising an olefin, carbon monoxide and hydrogen in the presence of a preformed catalyst at from about 100° to about 200° C. at a pressure of from about 500 psi to about 2500 psi and from between 0.5 to about 10 hours, said catalyst having the following general formula:

$$M^{+n}[H_yRu_xL_z]^{-n}$$

wherein
M is a cationic moiety;
n is an integer greater than or equal to 2;
x is an integer greater than or equal to 1;
L is a ligand; and
z is an integer less than or equal to the available coordination bonding sites of the Ru.

12. The method of producing a linear $C_4$–$C_{19}$ aldehyde comprising reacting an anhydrous mixture comprising a $C_3$–$C_{18}$ olefin, CO and hydrogen in the presence of a catalyst at from about 100° to about 200° C. at a pressure of from about 500 psi to about 2500 psi and from between 0.5 to about 10 hours wherein said catalyst has the following general formula:

$$M^{+n}[H_yFe_xL_z]^{-n}$$

wherein:
n represents an integer greater than or equal to 2;
M represents a cationic species;
y represents an integer greater than or equal to 0;
x represents an integer greater than or equal to 1;
L is a ligand; and
z represents an integer less than or equal to the available coordination bonding sites of the Fe.

13. The method of forming linear alcohols by reacting an olefin having at least three carbon atoms with carbon monoxide and a hydrogen source in the presence of a preformed catalyst at from about 100° to about 200° C. at a pressure of from about 500 psi to about 2500 psi and from between 0.5 to about 10 hours wherein said olefin has the following general formula:

$$R_1-\overset{\overset{H}{|}}{C}=\overset{\overset{H}{|}}{C}-R_2$$

wherein
$R_1$ is selected from the group consisting essentially of alkyl, substituted alkyl, aryl and substituted aryl, $R_2$ is selected from the group consisting essentially of hydrogen, alkyl, substituted alkyl, aryl and substituted aryl, and either $R_1$ or $R_2$ represents hydrogen or $C_1$–$C_9$ alkyl;
wherein said preformed catalyst has the following general formula:

$$M^{+n}[H_yA_xL_z]^{-n}$$

wherein
A represents a metal selected from the group consisting essentially of Fe, Ru and Os;
n represents an integer greater than or equal to 2 if A is Ru or Fe and n represents an integer greater than or equal to 1 if A represents Os;
M represents a cationic moiety;
y represents an integer greater than or equal to 0;
x represents an integer greater than or equal to 1;
L is a ligand; and
z is an integer less than or equal to the available coordination bonding sites of A.

14. The method claimed in claim 13 wherein $R_2$ represents hydrogen.

15. The method claimed in claim 14 wherein $R_1$ represents $C_1$–$C_{19}$ straight chain, unsubstituted alkyl.

16. The method claimed in claim 13 wherein $R_1$ and $R_2$ represent hydrogen or $C_1$–$C_9$ straight chain, alkyl.

17. The method claimed in claim 13 wherein the hydrogen source is hydrogen gas.

18. The method claimed in claim 13 wherein A represents Os.

19. The method claimed in claim 13 wherein A represents Ru.

20. The method claimed in claim 13 wherein A represents Fe.

21. The method of forming linear alcohols comprising reacting an olefin, carbon monoxide and hydrogen in the presence of a catalyst at from about 100° to about 200° C. at a pressure of from about 500 psi to about 2500 psi and from between 0.5 to about 10 hours wherein said catalyst has the following general formula:

$$M^{+n}[H_yOs_xL_z]^{-n}$$

wherein
M represents a cationic moiety;
n represents an integer greater than or equal to 1;
y represents an integer greater than or equal to 0;
x represents an integer greater than or equal to 1;
L is a ligand; and
z represents an integer less than or equal to the available coordination bonding sites of the Os.

22. The method of forming linear alcohols comprising reacting an anhydrous mixture comprising an olefin, carbon monoxide and hydrogen in the presence of a preformed catalyst at from about 100° to about 200° C. at a pressure of from about 500 psi to about 2500 psi and from between 0.5 to about 10 hours, said catalyst having the following general formula:

$$M^{+n}[H_yRu_xL_zL]^{-n}$$

wherein
M is a cationic moiety;
n is an integer greater than or equal to 2;
x is an integer greater than or equal to 1;
L is a ligand; and
z is an integer less than or equal to the available coordination bonding sites of the Ru.

23. The method of producing a linear $C_4$–$C_{19}$ linear alcohol comprising reacting an anhydrous mixture comprising a $C_3$–$C_{18}$ olefin, CO and hydrogen in the presence of a catalyst at from about 100° to about 200° C. at a pressure of from about 500 psi to about 2500 psi and from between 0.5 to about 10 hours wherein said catalyst has the following general formula:

$$M^{+n}[H_yFe_xL_z]^{-n}$$

wherein:
n represents an integer greater than or equal to 2;
M represents a cationic species;
y represents an integer greater than or equal to 0;
x represents an integer greater than or equal to 1;
L is a ligand; and
z represents an integer less than or equal to the available coordination bonding sites of the Fe.

24. The method claimed in claim 1 wherein L represents a ligand selected from the group consisting of trialkyl phosphenes, trialkyl arsenes, trialkyl antimonies, trialkyl bismuths, triaryl phosphenes, triaryl arsenes, triaryl antimonies, triaryl bismuths, carbon monoxide and tertiary amines.

25. The method claimed in claim 24 wherein m represents a cationic species selected from the group consisting of Group Ia and Group IIa metals and ammonium, phosphonium and arsenium.

* * * * *